US009078643B2

(12) United States Patent
Bleibach (10) Patent No.: US 9,078,643 B2
(45) Date of Patent: Jul. 14, 2015

(54) SAMPLING APPARATUS FOR TAKING A NUMBER OF SAMPLES

(75) Inventor: John Bleibach, Hellerup (DK)

(73) Assignee: Multi Biopsy Instruments ApS, Fredensborg (DK)

( * ) Notice: Subject to any disclaimer, the term of this patent is extended or adjusted under 35 U.S.C. 154(b) by 514 days.

(21) Appl. No.: 13/419,970

(22) Filed: Mar. 14, 2012

(65) Prior Publication Data

US 2012/0197156 A1   Aug. 2, 2012

Related U.S. Application Data

(63) Continuation of application No. 12/087,600, filed as application No. PCT/DK2007/000017 on Dec. 1, 2007, now abandoned.

(60) Provisional application No. 60/758,220, filed on Jan. 12, 2006.

(30) Foreign Application Priority Data

Jan. 12, 2006   (DK) .......................... PA 2006 00051

(51) Int. Cl.
| | |
|---|---|
| A61B 10/00 | (2006.01) |
| A61B 10/04 | (2006.01) |
| A61B 10/06 | (2006.01) |
| A61B 10/02 | (2006.01) |
| A61B 17/29 | (2006.01) |
| A61B 19/00 | (2006.01) |

(52) U.S. Cl.
CPC ............. *A61B 10/04* (2013.01); *A61B 10/06* (2013.01); *A61B 10/0096* (2013.01); *A61B 10/02* (2013.01); *A61B 10/0266* (2013.01); *A61B 19/38* (2013.01); *A61B 2010/0225* (2013.01); *A61B 2017/2926* (2013.01); *A61B 2017/2931* (2013.01)

(58) Field of Classification Search
CPC .... A61B 10/02; A61B 10/06; A61B 10/0096; A61B 2010/0225; A61B 2017/2926
See application file for complete search history.

(56) References Cited

U.S. PATENT DOCUMENTS

| | | |
|---|---|---|
| 5,782,747 A | 7/1998 | Zimmon |
| 6,071,248 A | 6/2000 | Zimmon |
| 6,832,990 B2 | 12/2004 | Kortenbach et al. |
| 7,588,545 B2 * | 9/2009 | Cohen et al. ............ 600/564 |
| 2003/0191413 A1 * | 10/2003 | Damarati ................ 600/567 |
| 2005/0256424 A1 | 11/2005 | Zimmon |

\* cited by examiner

*Primary Examiner* — Devin Henson
(74) *Attorney, Agent, or Firm* — Dykema Gossett PLLC (57) ABSTRACT

An apparatus for taking tissue samples in the treatment of humans or animals includes a telescope, a maneuvering cable which extends through the telescope, and a biopsy tool at an end of the maneuvering cable, the biopsy tool including a turnable cylinder which is perforated for collecting samples and has walls that define a receptacle and a lid which closes over the receptacle.

11 Claims, 9 Drawing Sheets

Fig. 23

SAMPLING APPARATUS FOR TAKING A NUMBER OF SAMPLES

CROSS-REFERENCE TO RELATED APPLICATIONS

This application is a continuation of application Ser. No. 12/087,600, filed Dec. 11, 2008 (now abandoned), which was a U.S. national stage filing of PCT/DK2007/000017, filed 12 Jan. 2007, which in turn claimed priority of Danish Application PA200600051, filed 12 Jan. 2006 and U.S. Provisional Application 60/758,220, filed 12 Jan. 2006. All priorities are requested.

BACKGROUND OF THE INVENTION

1. Field of the Invention

The invention relates to an apparatus for taking tissue samples and the like in the context of use of a kind of telescope for examination or treatment in the treatment of humans or animals, which apparatus is provided with a passage for advancing a maneuvering cable through the apparatus, the maneuvering cable being connectable to a tool for taking tissue samples and the like provided with a receptacle for accommodating tissue samples and the like.

2. Prior Art

In recent years it has become increasingly common to perform examinations and/or surgical interventions by using a kind of telescope. The advantage of using an examination and/or treatment telescope is that it is necessary to surgically open the patient only so much that there is space for introducing the examination and/or treatment telescope into the opening thus provided. It is also possible to use one of the natural orifices of the body for introducing the apparatus, e.g., in the context of an endoscopy, in particular when examining digestive tracts, optionally through the oesophagus, or when examining the digestive tracts through the rectum.

In the context of taking samples through such examination and/or treatment telescope (in the following designated the telescope), the so-called biopsy forceps are known that are a relatively thin and long, pliable device consisting primarily of an outer cable that extends throughout the expanse of the forceps, in which outer cable an internal maneuvering cable can be conveyed that connects an operating handle at the outer end of the biopsy forceps to a set of jaws at that end of the forceps that is taken through the telescope. By influencing the operating handle the jaws are moved in such a way that it is possible to cut off a sample of tissue and pull the tissue out along with the biopsy forceps. Often, such biopsy forceps have a length of between 1.5 m and 2 m. When biopsy forceps are introduced into the telescope, it is necessary, in the known appliance, to introduce them a small distance at a time, often about 5 cm. This means that the doctor carrying out the examination with his one hand must introduce the biopsy forceps 5 cm at a time and after having taken a tissue sample, he must carefully remove the biopsy forceps from the telescope again, still using his one hand while the other one keeps the jaws of the forceps closed around the tissue sample or the biopsy via the operating handle. This is a time-consuming process which is often a discomfort to the patient being examined/treated, not all examinations/treatments taking place under sedation. It is not uncommon for biopsy forceps to be moved about 1.4 m into the patient and out again, i.e., two times 1.4 m, during one single sampling.

In some examinations it is necessary to collect as many as ten samples for subsequent analyses. It is therefore very inconvenient to have to take biopsy forceps through the telescope ten times, which entails moving the forceps two times 14 m inside the patient.

It is therefore the object of the invention to provide an apparatus for sampling by which it is possible to take as many as about ten samples without having to insert and withdraw the forceps through the telescope and the patient for each sample that is taken. This also considerably reduces the possible risk of perforations to the intestine.

Apart from passages for sucking and flushing and a mini-camera for diagnostics and navigation, a telescope also features a passage for introducing the biopsy forceps. This passage is about 2.8 mm in diameter and the diameter of the existing biopsy forceps are typically 2.4 mm which provides a clearance when the biopsy forceps are introduced into the telescope.

Therefore, it is obvious that it is not possible to increase the diameter of the biopsy forceps too much, as it would render introduction into the telescope more cumbersome, which further entails that it will take considerably longer to take the biopsy forceps through the telescope and into the patient.

SUMMARY OF THE INVENTION

According to the invention this object is accomplished in that the apparatus for taking out tissue samples and the like is provided with a receptacle for accommodating tissue samples and the like where a sort of garage is provided in the telescope so as to avoid that the tool protrudes significantly during its insertion into the patient, or does not protrude at all.

Various kinds of tools can be used in connection with the telescope for performing other tasks. Such tools can be e.g., tools for positioning clamps, loops or the like and various examination tools or utensils therefore. It is a common feature that they can be exchanged and that they can be operated via the maneuvering cable.

A cap or rounded shield can be used so that the tool is not caught in folds or orifices inside the patient during introduction of the examination or treatment telescope into the patient. If, for instance, an out pouching were to be present on an intestine it would aggravate the situation if the equipment that is to relieve any suffering of the patient was able to penetrate such out pouching and cause a perforation of the intestine with ensuing increased suffering.

The cap or rounded shield can include a flexible slot or opening so that the tool can be taken from a passive transport position through the cover cap or shield to an active position from where the samples can be taken and collected.

The examination or treatment telescope can include a passage for a maneuvering cable and a bore at an end for insertion in a patient for partially or totally receiving the tool at the end of the cable.

The tool can include a receptacle containing an exchangeable foil, where, following ended sampling, the foil encloses the samples, the tests can be withdrawn collectively by the tool and be accommodated collectively in an accommodation receptacle for storage or for being handed over to a laboratory or the like.

The foil can be made of or include a coating which, as a safety measure, retains the collected sample(s) in the receptacle even if the receptacle is opened when new samples are taken.

The receptacle can include a lid which has a cutter or swipe means to cut off or swipe off a piece of tissue for taking a sample.

The receptacle can be rigid so that the comparatively rigid receptacle with samples therein can either be dismounted while containing the samples or emptied, cleaned and reused.

The receptacle can be perforated so that the receptacle can be closed off to the effect that the samples cannot drop out when the entire appliance is withdrawn from the patient again.

The lid can also be perforated to allow passage of liquid or the like, but not passage of the collected samples.

The receptacle can be a cylindrical unit with a cutter device formed of two essentially disc-shaped cutting parts. The cutting parts move within a cylindrical receptacle.

Passages can be provided in the tool and the telescope so that a sample can be taken or guided into the receptacle by means of suction and, despite suction applied to the tool, the samples remain in the receptacle and are not sucked into the cable.

The receptacle can be a turnable cylinder with a plurality of openings for samples so that several samples can be taken and stored in individual receptacles forming a single unit.

It is also possible to apply the technique to a capsule endoscopy, where it is intended that the patient swallows a capsule, which capsule passes through the intestines of the patient. During the passage pictures, video, can be recorded and scans performed of the internal organs and the like.

By providing such capsule with the tool described in the invention, where the tool is activated by manoeuvering means from/within the capsule, further options become available as to the undertaking of sample collections from the intestines of a patient in a convenient manner. Optionally, the capsule can be manoeuvered or directed through the patient by means of magnetic fields, remote control or the like wireless transmission. It is also conceivable that the transmission of control signals takes place through a cable which is withdrawn with great care from the patient along with the capsule, or, following ended use, the cable may be disconnected from the capsule and be pulled carefully out of the patient, following which the capsule proceeds out of the patient along the natural route.

BRIEF DESCRIPTION OF THE DRAWINGS

In the following, the invention will be described in further detail with reference to the drawings.

DETAILED DESCRIPTION OF THE PREFERRED EMBODIMENTS

Figure 1:
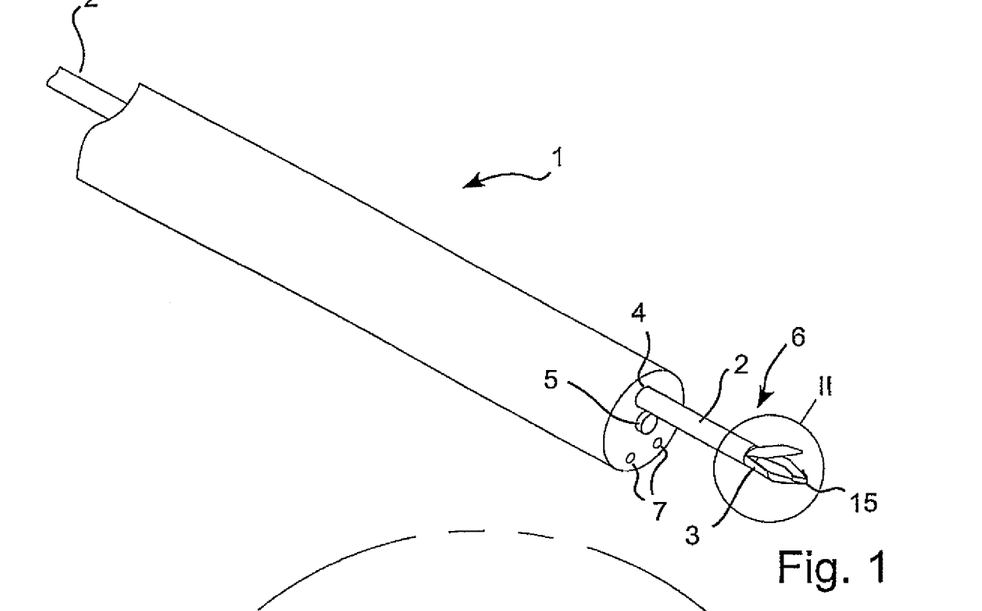
FIG. 1 shows an examination or treatment telescope, seen in a perspective view from the end which is introduced into the patient.
Figure 2:
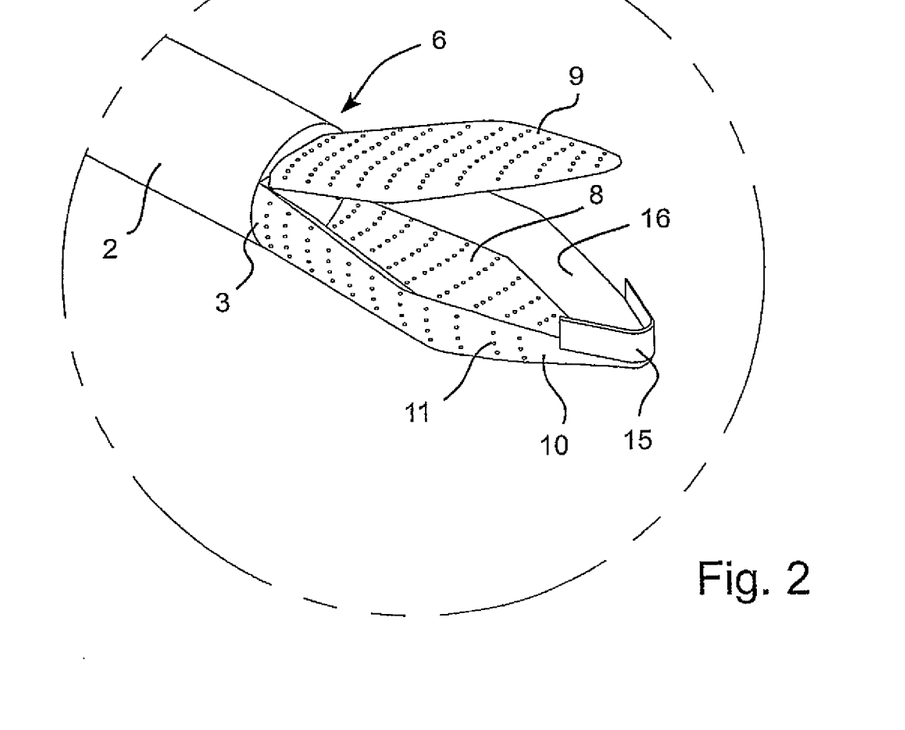
FIG. 2 shows a detailed view of a tool for the telescope shown in FIG. 1, indicated in area II.

Now convenient embodiments of the invention will be described. The apparatus, which is primarily used for taking tissue samples and the like in the context of use of a kind of telescope 1 for examination or treatment in the treatment of humans or animals, comprises a kind of manoeuvring unit 2 in the form of a cable or the like, which cable 2 comprises at least one inner part 21 and at least one outer part that can be moved relative to each other to the effect that a kind of tool 3 arranged at that end of the cable 2 which is, via the telescope 1, conveyed into a patient can be operated by influencing one or more operating handles arranged at that end of the cable 2 which is arranged at the end of the telescope 1 from where it is operated. In addition to a passage 4 for the operating cable 2 or the sampling cable, constituting in combination with the tool 3 a biopsy cable or biopsy forceps 6, this type of telescope 1 often comprises one or more passages 7 intended for sucking or flushing liquid or the like. At the end of the telescope 1, more specifically the end which is intended for being introduced into the patient, a camera 5 is arranged, whereby it is possible to see how the telescope 1 is to be moved during the introduction procedure and how the biopsy forceps 6 are to be moved to take the intended sample in the right place.

At the end of the cable 2 wherein the sample is to be taken, coupling means (not shown) are provided, which coupling means may be of ordinary type. The most important aspect is, in this context, that a tool 3 can be arranged at the end of the cable 2 in such a manner that it is easy to exchange if, in some situation or other, there is a need for attaching another type of tool 3 to the cable 2, and that the tool 3 can be secured in the cable in a reliable manner without falling off in use.

Figure 3:
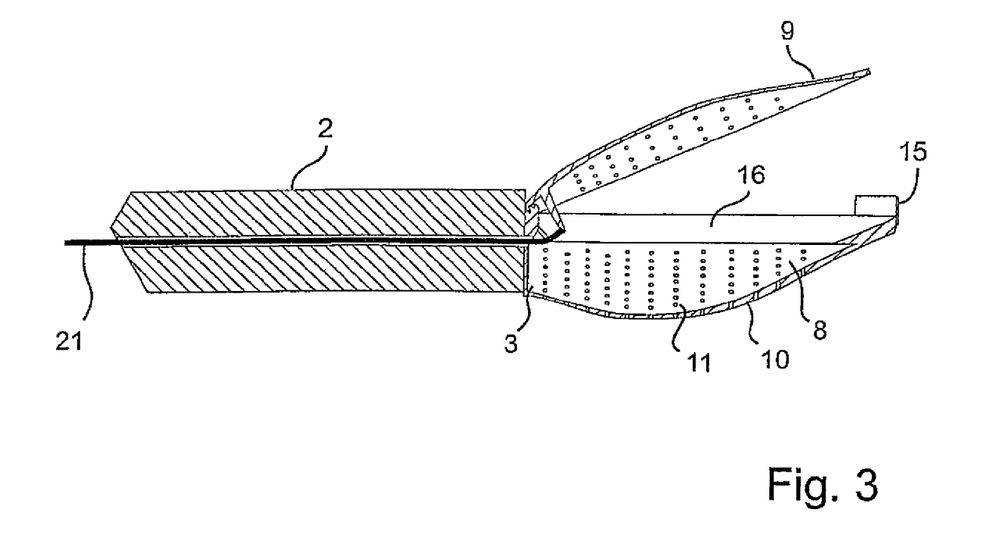
FIG. 3 shows a tool mounted on a biopsy cable and with open lid.
Figure 4:
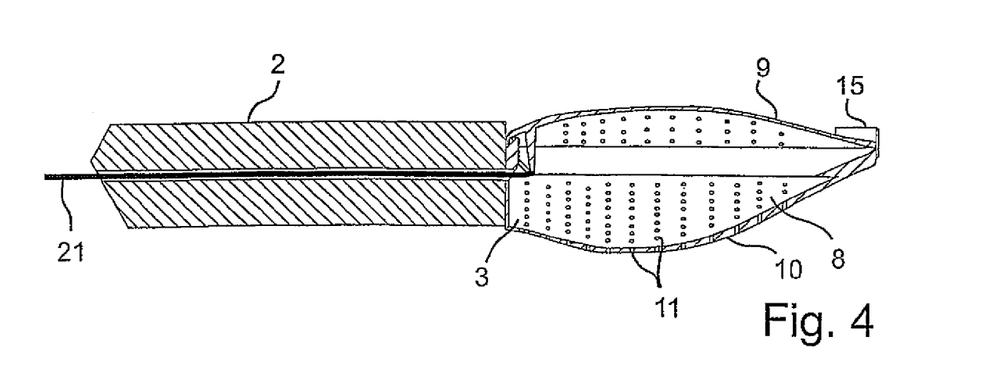
FIG. 4 shows a tool mounted on a biopsy cable and with closed lid.

In a preferred embodiment, the tool 3 comprises a receptacle 8 and a lid 9, which lid 9 is activated by means of control via the cable 2 or by other means to open or close to the effect that a sample can be collected, arranged in the receptacle 8, following which a new sample can be collected and arranged in the receptacle 8. This sequence can be repeated as often as needed for the sake of number of samples for as long as there is still space available to the samples in the receptacle 8. It is important that, during withdrawal of the telescope 1 from the patient, the samples remain in the receptacle 8.

Expediently, the receptacle is dimensioned to be able to accommodate as many as 20 samples, preferably about 10.

The receptacle 8 can be constituted of a kind of framework (not shown) which is able to stretch and secure a foil, which foil can in turn be released from the framework again following ended sampling. Thereby it is accomplished that the samples just taken and arranged in the foil and with the telescope withdrawn from the patient can be exchanged along with the foil in a suitable liquid, such as formalin or the like, until the sample is analysed. The receptacle and/or tool can be sent as a unit for analysis and reused, or receptacle and/or tool can be disposable.

According to a further embodiment receptacle 8 and lid 9 are configured with walls 10 of a comparatively rigid material. In the walls 10, openings 11 are configured, said openings 11 being of such size that a liquid is able to flow in and out through the openings 11, whereas a sample accommodated in the receptacle 8 cannot pass through such opening 11.

According to a further embodiment of receptacle 8 and lid 9, they can be configured as frames with a mesh secured thereto for providing the above through-flow and retention. Finally a lid 9 and a receptacle 8 can be configured by combinations of said embodiments.

Figure 7:
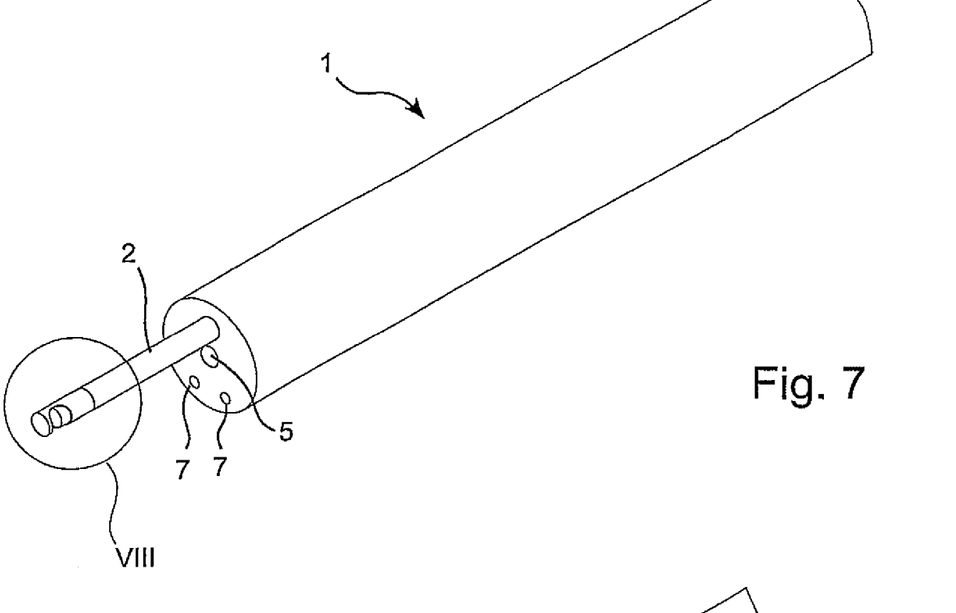
FIG. 7 shows an embodiment of a tool for collecting and temporarily accommodating tissue samples.
Figure 8:
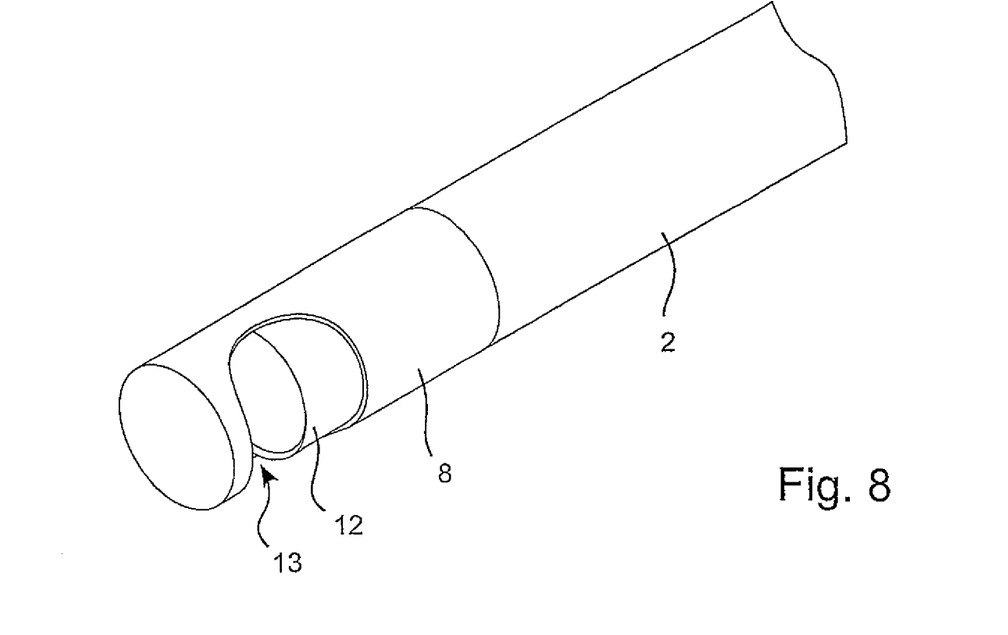
FIG. 8 shows a detailed embodiment of the tool for collecting and temporarily accommodating tissue samples indicated by VIII in FIG. 7.
Figure 9:
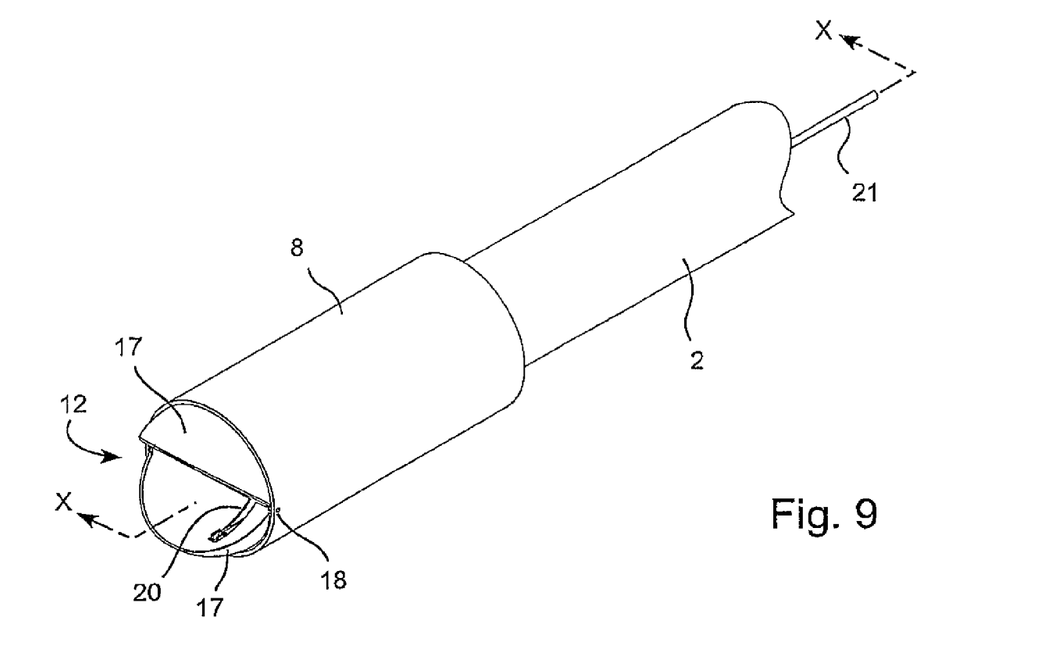
FIG. 9 shows an embodiment of a tool with dish-shaped cutting parts.
Figure 10:
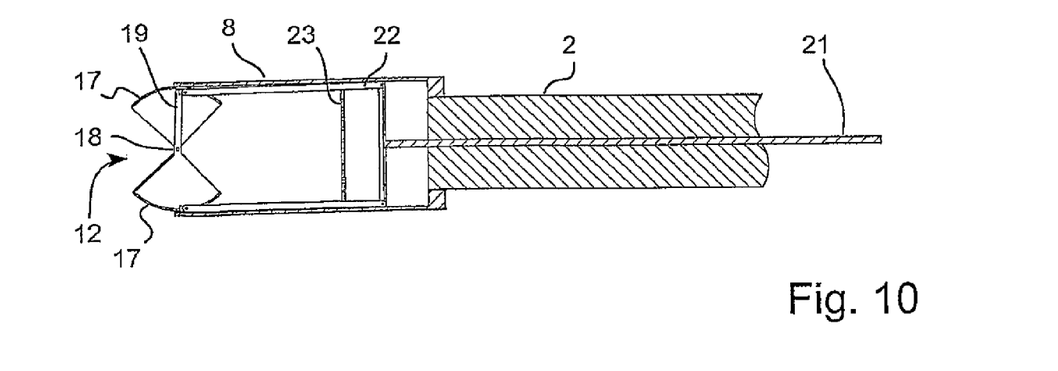
FIG. 10 shows the embodiment shown in FIG. 9, seen along section X-X.
Figure 11:
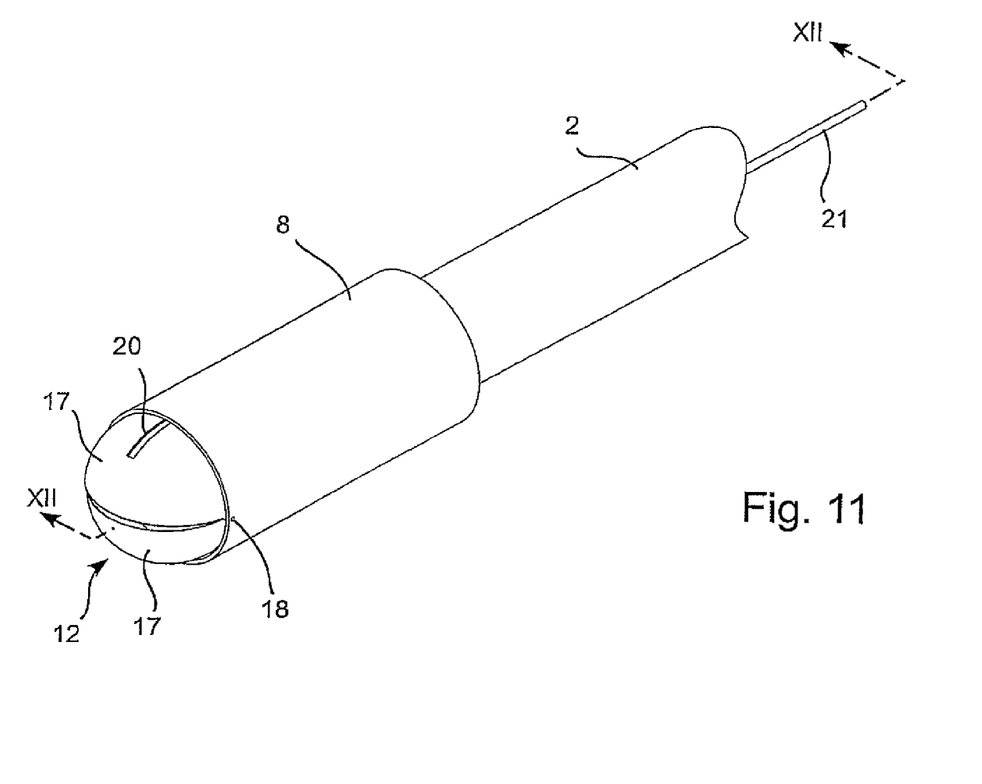
FIG. 11 shows a further embodiment of a tool with dish-shaped cutting parts.
Figure 12:
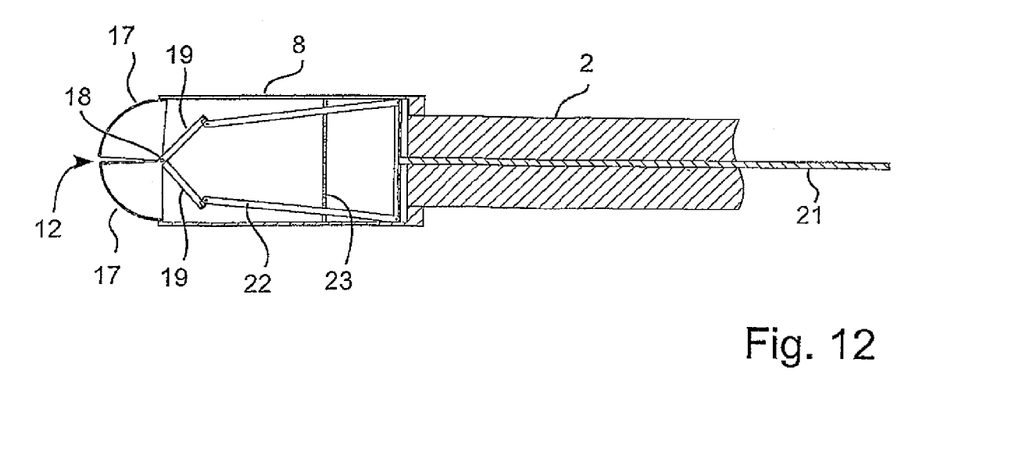
FIG. 12 shows the embodiment of FIG. 11, seen along section XII-XII.

According to yet an embodiment of lid 9 and receptacle 8, they can be configured as an elongate cylinder 8, in which cylinder 8 a kind of cutter 12 can be taken along the inside of the cylinder 8 in a longitudinally extending direction or in a direction extending along the inner periphery, to the effect that the cutter 12 can be caused to cover an opening 13 provided in the sidewall of the cylinder 8. Hereby it is accomplished that, apart from cutting off a sample such that it falls into the cylinder or receptacle 8, the cutter 12 also serves as a lid 12 meaning that the sample is unable to fall out of the receptacle again. This embodiment which is also an exchangeable tool may, like the embodiments mentioned above, be provided with perforations to the effect that liquid is able to pass through lid and/or receptacle, whereas the samples are unable to pass.

In this embodiment the cylinder 8 can optionally be configured to be so elongate that it can be caused to have such small diameter that it is possible for such cylinder 8 to pass through a passage 3 in the telescope 1 along with the biopsy forceps 6 and be secured at the end of the cable 2.

According to a further development of this embodiment, the cutter or cutting part can be constituted of two essentially dish-shaped cutting parts 17, both of which are shaped like a part of a spherical shell and hinged 18 mutually close to the periphery that appears when the cutting parts 17 are in their closed position. Thereby it is obtained that the cutting parts 17 do not increase their mutual outer diameter, when the cutting parts 17 are opened and closed. The cutting parts 17 are able to close with cutting edge towards cutting edge or the cutting parts 17 may close overlapping.

By providing in connection with the cutting parts 17 a reaction lever 19 connected to each cutting part 17, said lever 19 being able to pass into a groove 20 formed in the rear of the cutting part 17, it is accomplished that, by pull in the inner cable 21, a force is applied to the cutting parts 17 in the closing direction of the cutting parts 17. The levers are connected to the inner cable 21 by means of a kind of yoke 22 that endeavour to ensure that forces are transferred equally between the cutting parts 17 when they are used to take a sample. At the most distal part of the receptacle 8, a kind of mesh or grid 23 is provided to ensure that the samples remain in the receptacle 8, if the manoeuvring cable 2 is provided with suction and/or flush.

The cylinder face of the receptacle as such can also be provided with perforations to allow liquid to pass without the samples being able to pass.

According to an alternative embodiment, the telescope 1 can be provided with a kind of cover cap (not shown), said cap being used to prevent the tool 3 from possibly perforating a wall of an intestine or the like. The cap, which is arranged on the inlet end of the telescope 1, is preferably transparent, but a kind of window may also be provided in the cap, through which the camera 5 is able to take pictures. Optionally the camera 5 can be secured in the cap, or it is possible to arrange means between the window in the cap and the camera for transferring the object to the camera 5.

In the cap, an opening or a flexible slot is provided such that, when the tool is to be brought from a passive position to an active position, it is able to pass through the cap and, following ended use, return to the passive position underneath the protective or covering cap.

According to one embodiment of this, it is an option to provide, at the end of the telescope 1 and within the cap, a collection receptacle for accommodating the collected samples to the effect that it is possible, by using ordinary biopsy forceps, to collect a sample, pour the sample into the receptacle, collect another sample, pour it into the receptacle and so on, until an acceptable number of samples have been collected. Then telescope 1 with samples is withdrawn from the patient.

Figure 5:
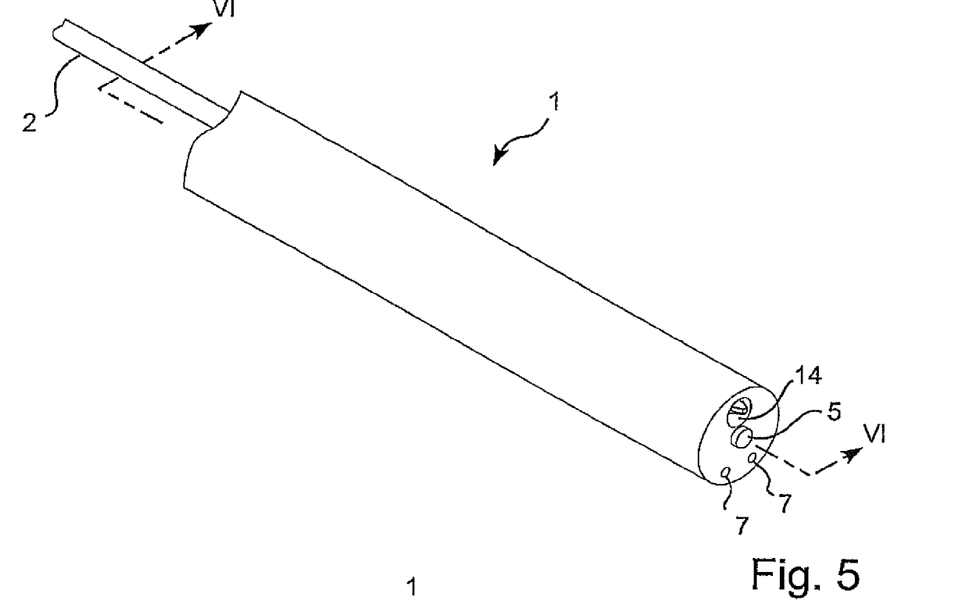
FIG. 5 shows the telescope, seen from the end, with no tools arranged in a kind of 'garage'.
Figure 6:
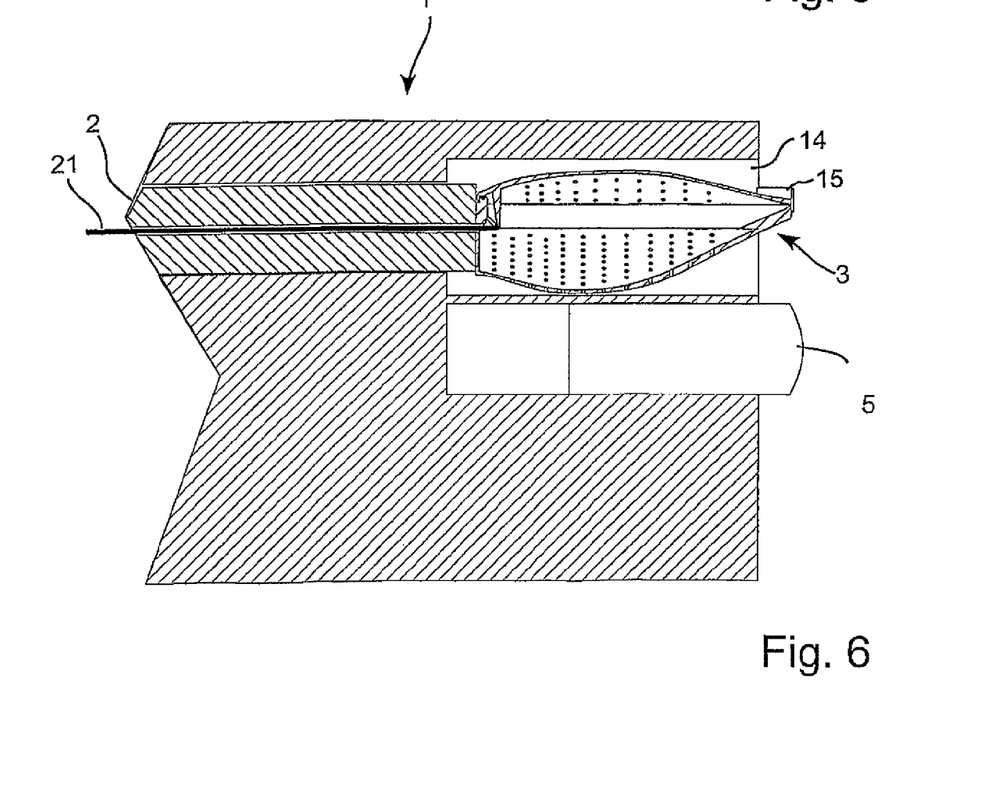
FIG. 6 shows the telescope in section VI-VI indicated in FIG. 5 and with a tool arranged in the 'garage'.

By providing a bore 14 or the like measure to increase the diameter of the passage 4 in the telescope 1 at that end of the telescope 1 which is intended for being introduced into the patient, a kind of 'garage' is accomplished in which the tool 3 can be accommodated during introduction into and withdrawal of the telescope 1 from the patient.

The bore 14 can be used to advantage in that the tool 3 is mounted on the cable 2 following conveyance of the cable 2 through the cable passage 4. Then the cable 2 is withdrawn so far back that the tool 3 is completely or partially encircled by the bore 14.

In connection with the tool 3, means 15 are provided for cutting off, clipping off or the like to separate a tissue sample from the patient's tissue. These means 15 may be in the form of a cutter, scissors or the like and may be arranged on the edge of the receptacle 6, on the edge of the lid 9 or as a combination thereof. A cutting edge 15 can also be moved in a guide configured in the immediate vicinity of the opening of the receptacle 8.

Moreover the receptacle 8 may be provided with an edge 16 at least along a portion of the opening of the receptacle 8, said edge 16 extending towards the centre of the receptacle opening. It is the purpose of that edge 16 to withhold the collected samples in the receptacle 8 so as to ensure that they do not unintentionally fall out the receptacle, when the lid is open eg during collection of a further sample.

According to a further embodiment of the edge 16, the edge 16 can be configured such that, in addition to extending towards the centre of the receptacle opening, it also extends at an angle towards the receptacle bottom to ensure improved retention of collected samples.

In an embodiment of connecting the operating cable 2 to the tool 3 a connecting lever 23 is provided with a hole 24 which is closed in the one end. At the side of the open end of the hole 24 a first slot or aperture 25 is provided and at a distance from the open end of the hole 24 a second slot or aperture extends from the first slot and in a plane perpendicular to the center axis of the hole. Hereby it is possible to insert the end of the inner cable 21 carrying a ball or cylindrical knob 26 into the lever 23 mostly similar to connecting a handbrake cable to the handbrake lever i.e. on a bicycle. When the cable is inserted in the first slot the cable 2 form an angle with the lever 23. By turning the cable 2 into a position in extension of the lever the inner cable 21 of the operating cable 2 is connected to the lever 23. To secure the outer part of the cable 2 to the tool 3 the tool 3 and cable 2 can be provided with mutual engaging treading parts, a bayonet coupling or, the like. The embodiments shown in FIGS. 13 to 18, 22 and 23 have mutual engaging treading parts.

Figure 13:
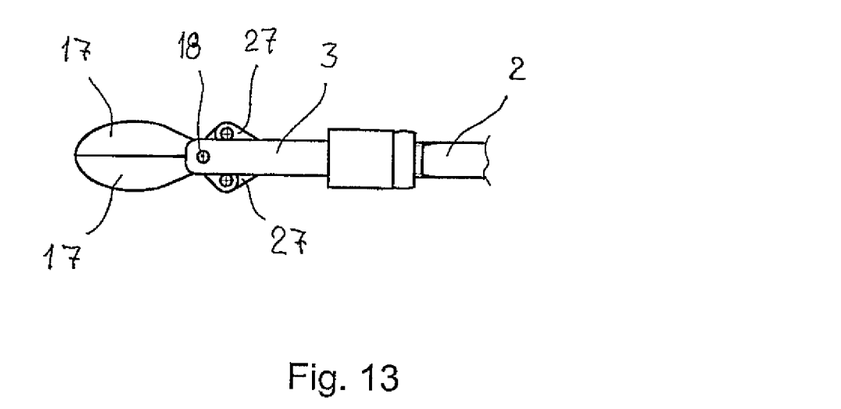
FIG. 13 shows another embodiment of a tool with dish-shaped cutting parts, the tool connected to the cable.
Figure 14:
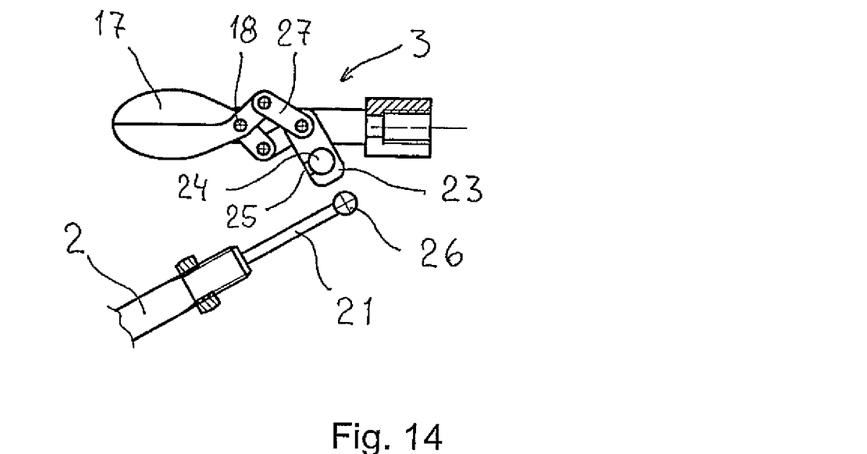
FIGS. 14-17 shows the embodiment of FIG. 13, the cable being connected to the tool and operating the tool, the tool with a securing nut shown in part sectional view.
Figure 15:
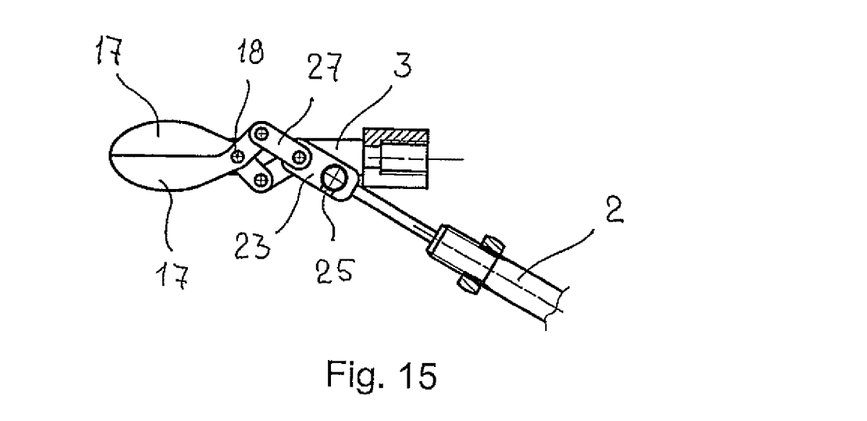
Figure 16:
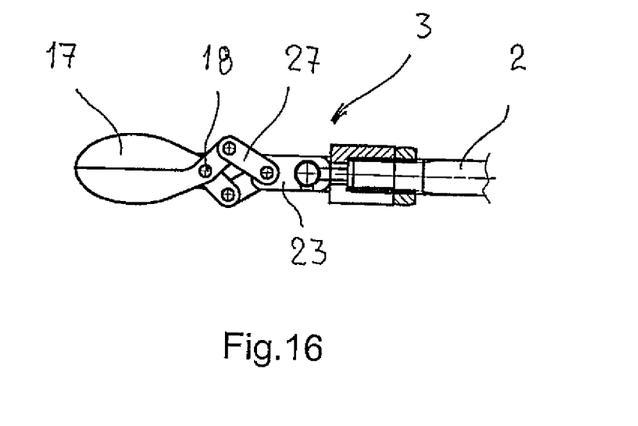
Figure 17:
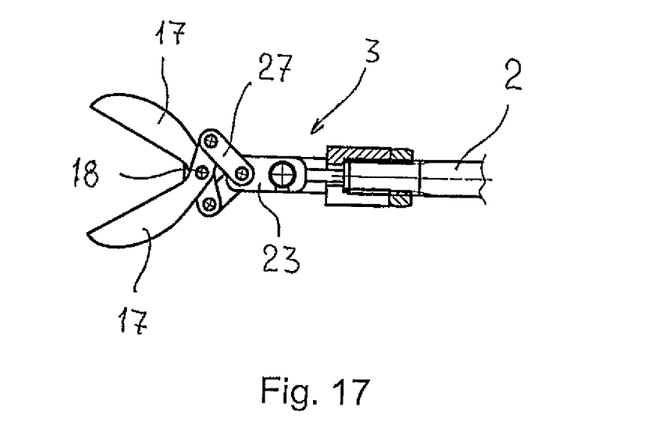

With the cable knob 26 inserted and the cable 2 turned into position and fastened to the tool 3 a stable and secure connection is obtained.

The tool are in this embodiment provided with two essentially dish-shaped cutting parts 17 connected to each other by a hinge 18. Each cutting part being connected to the connecting lever 23 by connecting links 27.

Figure 18:
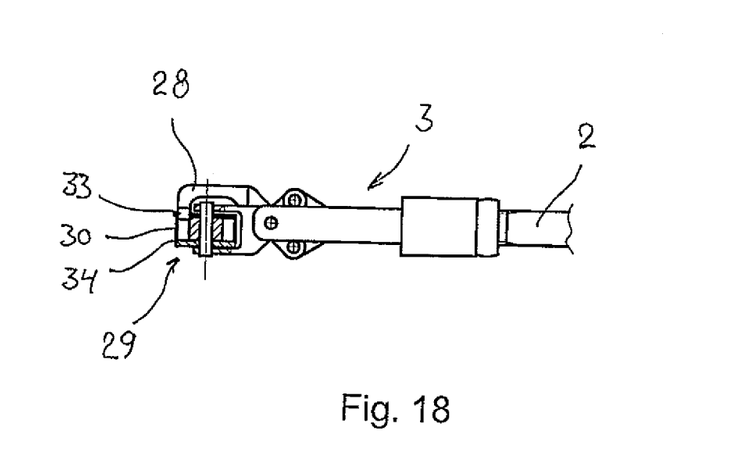
FIG. 18 shows the tool with a further embodiment of the receptacle.
Figure 19:
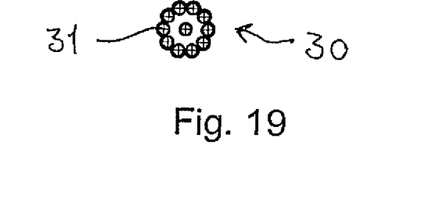
FIG. 19 shows the embodiment of the receptacle of FIG. 18, formed as a cylinder with a plurality of receptacle openings.

In a further development of this embodiment the two essential dish-shaped cutting parts are replaced by a tonglike arm 28 and a receptacle arm 29 comprising a cylinder 30 with a plurality of openings 31, the tonglike arm 28 and the receptacle arm 29 being hinged to each other. When these two parts are moved towards each other operated by the cable 2 a sample is taken and placed i the receptacle 30. The receptacle is formed like a drum for a revolver, forming a plurality of chambers suitable to contain a sample in each opening. It is obvious, that the number of openings used for collecting samples depends on the needed number of samples.

Figure 20:
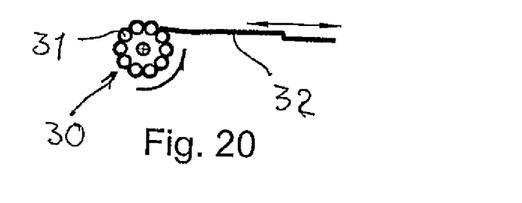
FIG. 20 shows a way to advance the receptacle.
Figure 21:
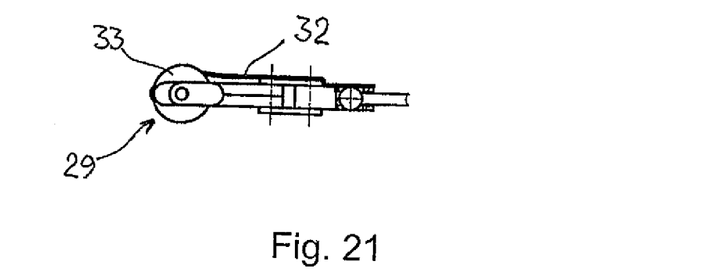
FIG. 21 shows a top view of the receptacle placed in the tool with the advancing mechanism.

In relation to the operating cable 2 an advancing mechanism 32 can be provided to advance the cylinder to the next opening before taking the next sample. The advancing of the cylinder 30 can be operated of the operating cable 2 or by another mechanism.

On top and under the receptacle formed as a cylinder with a plurality of openings, two discs 33, 34 can be placed. The disc 33 at the top is arranged with an opening placed in relation to the receptacle in such a way that the opening is situated above one of the receptacle openings. The top disc 33 is preferably in a fixed position relative to the tool 3. The hole in the top disc 33 is arranged with a cutting edge along its circumference (not shown).

The cylinder 30 is held in position after advancing by means for locking the cylinder, such as a latch, a flat spring or the like (not shown).

Figure 22:
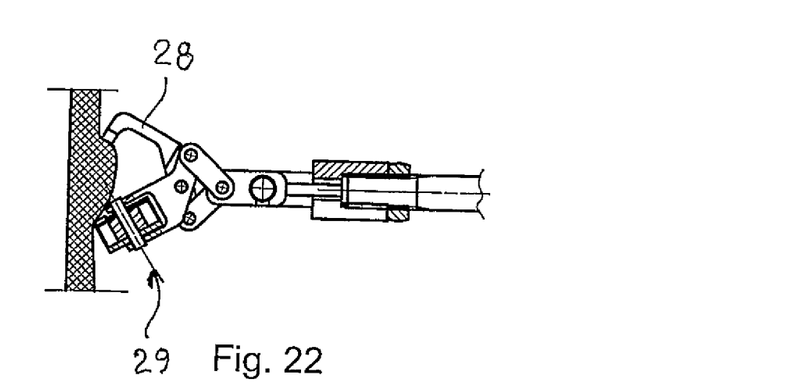
FIGS. 22 and 23 shows the tool with the receptacle of FIG. 18 taking a sample and placing it in one of the openings in the receptacle.
Figure 23:
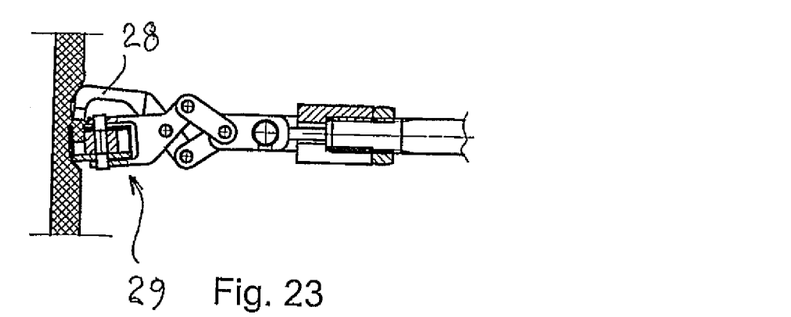

Thereby it is possible to place a sample directly when taken into the selected opening in the receptacle. When taking the next sample, the cylinder is advanced or revolved in such a way that the next opening in the cylinder is arranged in relation to the top disc so that the previous sample is held in a closed state and the opening in the cylinder, which opening is ready to receive the next sample is situated aligned with the opening in the top disc leaving the opening available.

In a further embodiment of the telescope the opening or "garage" suitable for storing the tool during introducing the telescope into the patient can be provided in the centre region of the end of the telescope. The opening can be a cylindrical hole or opening or the opening can show the shape of a cross, a T or the like, thereby leaving sufficient of surrounding material to position suction- and/or flushing-channels, camera and the like.

It is clear that the invention can be combined across the embodiments of the invention.

In connection with the various embodiments of the tool 3, it is an option to provide, at that end of the tool 3 that faces towards the coupling means of the cable, connection to suction and/or flushing passages 7, either via passages within the telescope 1 or via coupling in at the manoeuvring end of the telescope of the biopsy cable. In order to ensure that the samples are not drawn out of the cable 2 and possibly damaged, it is an option to arrange a kind of mesh or grid at the coupling end of the tool 3, said grid or mesh featuring a passageway for the operating cable for the tool.

The individual tools that can thus be arranged at the end of a biopsy cable may have different dimensions adapted to the task for which the tool is used.

The invention claimed is:

1. An apparatus for taking tissue samples of a human or animal, comprising a treatment telescope having an end to be introduced into a patient, and a biopsy tool operable at said end to separate tissue samples from the tissue, wherein the biopsy tool has a first arm and a second arm and a turnable cylinder at said end, wherein the turnable cylinder is a receptacle for tissue samples and comprises a plurality of openings for collecting the samples, wherein the turnable cylinder is turnable about an axle on the first arm, and wherein said axle on the first arm is movable with the first arm towards the second arm.

2. The apparatus according to claim 1, wherein on top of the turnable cylinder a disc is arranged with an opening in the disc located above one of the openings in the receptacle.

3. The apparatus according to claim 2, wherein the opening in the disc has a cutting edge along its circumference.

4. The apparatus according to claim 2, wherein the cylinder is turnable with respect to the disc.

5. The apparatus according to claim 4, wherein an advancing mechanism can turn the cylinder to align a next opening in the cylinder with the opening in the disc.

6. The apparatus according to claim 5, wherein the cylinder is lockable in position.

7. The apparatus according to claim 1, wherein the turnable cylinder on the first arm of the biopsy tool and the second arm of the biopsy tool are movable towards each other by the maneuvering cable.

8. The apparatus according to claim 1, wherein the receptacle comprises a closing mechanism to open and close off access to openings in the receptacle.

9. The apparatus according to claim 1, wherein at least a portion of the opening is provided with an edge arranged to retain a collected sample.

10. The apparatus according to claim 1, wherein the turnable cylinder and the second arm on the biopsy tool are connected to a maneuvering cable.

11. The apparatus according to claim 1, wherein the first arm and the second arm are hinged to each other.

* * * * *